(12) United States Patent
Wong

(10) Patent No.: US 7,192,423 B2
(45) Date of Patent: Mar. 20, 2007

(54) DISPENSING SPIKE ASSEMBLY WITH REMOVABLE INDICIA BANDS

(76) Inventor: Cindy Wong, 103 Falcongate Dr., Monmouth Junction, NJ (US) 08852

( * ) Notice: Subject to any disclaimer, the term of this patent is extended or adjusted under 35 U.S.C. 154(b) by 357 days.

(21) Appl. No.: 10/991,027

(22) Filed: Nov. 17, 2004

(65) Prior Publication Data

US 2006/0106360 A1 May 18, 2006

(51) Int. Cl.
*A61B 5/15* (2006.01)
*A61M 37/00* (2006.01)

(52) U.S. Cl. .................................. 604/411; 604/188

(58) Field of Classification Search ........ 604/411–413, 604/404–406, 6.12, 188, 240; D24/112, D24/130; 206/571
See application file for complete search history.

(56) References Cited

U.S. PATENT DOCUMENTS

| | | | |
|---|---|---|---|
| 1,411,542 A | 4/1922 | Van Orsdale | |
| 1,517,132 A | 11/1924 | Tieck | |
| 3,092,106 A | 6/1963 | Butler | 128/214 |
| 3,160,322 A | 12/1964 | Burnett | 222/88 |
| 3,258,168 A | 6/1966 | Koehler, Jr. | 222/88 |
| 3,316,908 A | 5/1967 | Burke | 128/214 |
| 3,783,895 A | 1/1974 | Weichselbaum | 137/588 |
| 3,868,965 A | 3/1975 | Noiles et al. | 137/559 |
| 3,885,562 A * | 5/1975 | Lampkin | 604/189 |
| 4,018,223 A * | 4/1977 | Ethington | 604/207 |
| 4,256,132 A * | 3/1981 | Gunter | 137/14 |
| 4,262,671 A | 4/1981 | Kersten | 128/272.3 |
| 4,750,643 A | 6/1988 | Wortrich | 222/81 |
| 4,834,744 A | 5/1989 | Ritson | 604/411 |
| 4,857,068 A * | 8/1989 | Kahn | 604/405 |
| 5,445,630 A | 8/1995 | Richmond | 604/411 |
| 5,741,242 A * | 4/1998 | Kriesel | 604/403 |
| 6,692,478 B1 | 2/2004 | Paradis | 604/403 |

OTHER PUBLICATIONS

InfuSafe—Simply Better Infusing Products: Needle-Free Vial Enclosure; http://www.infusafe.com/vial_closure.jsp; Apr. 21, 2004; p. 1 and 2.
InfusingSolutions.com AS50 Auto Syringe Infusion Pump; http://infusingsolutions.com/Products/Interlink.html; Feb. 2, 2004; copyright 1995-2002 Baxter Healthcare Corporation, Becton Dickinson Division; p. 1.

\* cited by examiner

*Primary Examiner*—Tatyana Zalukaeva
*Assistant Examiner*—Laura C. Hill
(74) *Attorney, Agent, or Firm*—Kenneth Watov; Watov & Kipnes, P.C.

(57) ABSTRACT

A spike assembly for facilitating the supply of a fluid from a container to a hypodermic syringe, fluid conduit extending therethrough between first and second ends of a body, a piercing member located at the first end for piercing into the container to form a fluid sealing engagement therebetween, a fluid seal, and a vent having a plurality of preprinted indicia bands with protective removable covers disposed around the outside surface of the vent which corresponds to a user details of the container contents.

11 Claims, 7 Drawing Sheets

DISPENSING SPIKE ASSEMBLY WITH REMOVABLE INDICIA BANDS

FIELD OF THE INVENTION

The present invention relates generally to dispensing device, and more particularly to dispensing spike assembly for facilitating the drawing of fluid into a syringe from a vial.

BACKGROUND OF THE INVENTION

One of the most common forms of drug delivery is parenteral administration, which is typically implemented through the use of a hypodermic syringe. Certain therapeutic and medicinal agents have to be administered via a syringe into the blood stream of a patient. Generally, the therapeutic agents are stored in glass vials capped with a resealable resilient membrane such as, for example, a rubber stopper. The hypodermic syringe is composed generally of a hollow pointed needle, a cylinder defining a reservoir in communication with the needle, and a plunger slidably located within the cylinder at the opposite end from the needle. The plunger is movable to draw into and expel fluid from the reservoir through the needle. The resealable rubber stopper is adapted to receive the needle of the syringe and form a fluid seal around the exterior portion of the needle.

The steps for directly drawing fluid contents from the vial into a syringe are well known. More specifically, prior to inserting the syringe into the vial, the plunger is drawn back to draw air into the syringe until the tip of the plunger reaches the line of the number of units required. The rubber stopper of the vial is wiped with an antiseptic. With the vial maintained in an upright position, the syringe needle is then pushed through the rubber stopper. The plunger is then pressed to expel the air into the vial. The vial and syringe is upturned bottom side up with the needle in the fluid. The syringe plunger is drawn back until it is at the appropriate line for the dose needed.

One problem in the prior art is that when a needle must be inserted into a vial to load the syringe with the fluid, in applications where a plurality of doses are obtained from the same vial, it is very difficult to avoid wasting a portion of the medication. When the fluid reaches a critical level, the user must often maneuver the needle tip below the fluid level to catch the fluid. Otherwise, the vial is typically discarded with a portion of the fluid still present, thus resulting in waste. A further problem is the use of needles to withdraw fluid from a container, which increases the likelihood of accidents involving inadvertent pricking. Another problem in the prior art is that vials filled with medication must be kept or stored within specific temperature ranges such as, for example, room temperature or refrigeration temperature. It is important that the health care provider be provided a readily observable notice as to storage requirements for a vial of medication after dispensing to a syringe.

Yet another problem requiring solution is to provide users of vials containing multiple doses of medication, for example, a way to maintain an indication of the original starting level of the medication or fluid, with the vial upright, before a first dose is withdrawn, to "eyeball" how many doses remain after each dose drawing.

Accordingly, there is a need for a spike assembly that can be operatively engaged to a fluid-containing vial in a manner, which effectively minimizes or eliminates the problems associated with prior art dispensing methods. There is a further need for a spike assembly that enhances the relative ease and promptness of dispensing fluids for drawing into a hypodermic syringe, while substantially minimizing waste and contamination of the fluid, and providing a readily observable notice of storage requirements and/or light sensitivity precautions. There is a further need to design a spike assembly having a removable port adapted to receive a hypodermic needle, which permits compatible use of the spike assembly with syringes outfitted with or without a hypodermic needle.

SUMMARY OF THE INVENTION

The present invention relates generally to a spike assembly useful for facilitating the dispensing of a fluid (typically a medication) from a vial to a fluid passing device such as a hypodermic syringe, maintaining the proper storage temperature and/or light sensitivity of the vial, reducing accidental needle pricking, and minimizing waste of the fluid. Typically, the vial includes a self sealing resilient membrane such as, for example, a rubber stopper, through which the spike assembly accesses the fluid. The spike assembly is adapted to be fluidly coupled with a fluid containing vial to form a fluid sealing engagement therebetween, thereby preventing or at least substantially minimizing undesirable leakage and contamination. The spike assembly includes a fluid conduit adapted to receive the needle or fluid port of a hypodermic syringe at one end, and at the other end for drawing fluid from the vial into the conduit therefrom into the needle or fluid port, rapidly and conveniently. Alternatively, the spike assembly can include a Luer lock fitting for coupling directly to a Luer lock port fitting of a syringe in the absence of a needle. The spike assembly of the present invention enhances the relative ease and promptness of dispensing fluids from a vial into a hypodermic syringe and promptly identifying the contents of a container, while substantially minimizing accidental needle prick, and reducing waste and contamination of the fluid.

The spike assembly of the present invention generally includes a body having an open first end, a second end, and a fluid conduit extending between the first and second ends. The first end includes a piercing member designed to puncture through the resilient membrane of the vial to gain access to the fluid contained in the vial. Once accessed, the vial can be turned or rotated bottom up to cause the fluid to enter the fluid conduit through the open first end of the spike assembly. The second end may be operated either in an open state or in a closed state. In the closed state, the second end is adapted to receive the needle of the hypodermic syringe where a fluid seal is formed around the received needle to prevent leakage during dispensing from the fluid conduit. In the open state, the second end is adapted to receive a needleless syringe for fluid coupling therebetween.

With the vial rotated to an upturned vertical position, the fluid in the vial enters the fluid conduit in contact with the needle. As the plunger of the syringe is drawn back to a desired dosage mark, the fluid is drawn from the fluid conduit via the needle into the syringe.

In one aspect of the present invention, there is provided a spike assembly for facilitating the supply of a fluid from a container to a fluid drawing device including a hypodermic syringe, the spike assembly comprising:

a body having a first end and a second end, and a fluid conduit extending therethrough between the first and second ends;

a piercing member located at the first end for piercing into the container to form a fluid sealing engagement therebetween, the piercing member further including means for passing the fluid into the first end from the container into the fluid conduit; and means located at the second end for receiving a fluid port or a needle of the fluid drawing device to enable the fluid drawing device to be operated to draw the fluid from the container via the fluid conduit, the receiving means providing a fluid seal about the fluid port or the needle where it passes through the receiving means.

In another aspect of the present invention, there is provided a spike assembly for facilitating the supply of a fluid from a container to a fluid drawing device including a hypodermic syringe, the spike assembly comprising:

a body having a first end and a second end, and a fluid conduit extending therethrough between the first and second ends;

a piercing member located at the first end for piercing into the container to form a fluid sealing engagement therebetween, the piercing member further including means for passing the fluid into the first end from the container into the fluid conduit;

means located at the second end for receiving a fluid port or a needle of the fluid drawing device to enable the fluid drawing device to draw the fluid from the container via the fluid conduit, the receiving means providing a fluid seal about the fluid port or the needle where it passes through the receiving means; and means located on the body for venting gas between ambient and the interior portion of the container during operation.

In a further embodiment of the present invention, the spike assembly may further include means for selectively indicating storage requirements including temperature and/or light sensitivity for the fluid or medication contained in the container.

Optionally, the spike assembly of the present invention may further include a drain aperture positioned near the point of entry inside the container, said drain aperture being in fluid communication with the fluid conduit.

BRIEF DESCRIPTION OF THE DRAWINGS

Various embodiments of the invention are described in detail below with reference to the drawings, in which like items are identified by the same reference designations, wherein.

DETAILED DESCRIPTION OF THE INVENTION

The present invention is directed to a spike assembly adapted for facilitating the dispensing of fluids, typically a medication, from a fluid container or a vial into syringes or other fluid drawing devices. The spike assembly provides protection against inadvertent spillage or fluid leakage from the vial during dispensing and storage. The spike assembly of the present invention is adapted to form a sealing engagement with the vial to maintain the fluid content in a sterile germ free condition, while enhancing the ease at which the fluid is dispensed into the syringe. The spike assembly of the present invention further functions to minimize introduction of potential contaminants into the vial being dispensed and reduces waste of the fluid.

The spike assembly is designed to be compatible for use with needle and needleless syringes or other fluid drawing devices. Accordingly, when used in conjunction with a needleless fluid drawing device (e.g., hypodermic syringe without needle attached), the spike assembly advantageously eliminates the probability of accidental or inadvertent pricking or jabbing during dispensing that may imperil the health and safety of the user.

The spike assembly can further be adapted to allow the user to readily identify the contents and/or storage temperature, and/or provide an indication of light sensitivity of the fluid to be dispensed by including a visual marker(s) or indicator(s) that can be easily implemented by the user. In this manner, the user can simply glance at the visual marker (s) without having to read the label directly affixed on the vial. The present spike assembly, in its various embodiments, is simple and cost effective to make using existing fabrication techniques as known in the art, and can be fabricated in a disposable form, thus making it especially suitable for use in the medical and pharmaceutical industry.

The spike assembly of the present invention generally includes a body having a first end and a second end, and a fluid conduit extending therethrough between the first and second ends. The spike assembly further includes a piercing member located at the first end for piercing into the vial to form a fluid sealing engagement therebetween, wherein the piercing member further includes means for passing the fluid into the first end from the vial into the fluid conduit, and means located at the second end for receiving a fluid port or a needle of the hypodermic syringe to enable the hypodermic syringe to draw the fluid from the vial via the fluid conduit, the receiving means providing a fluid seal about the fluid port or the needle where it passes through the receiving means.

Figure 1:
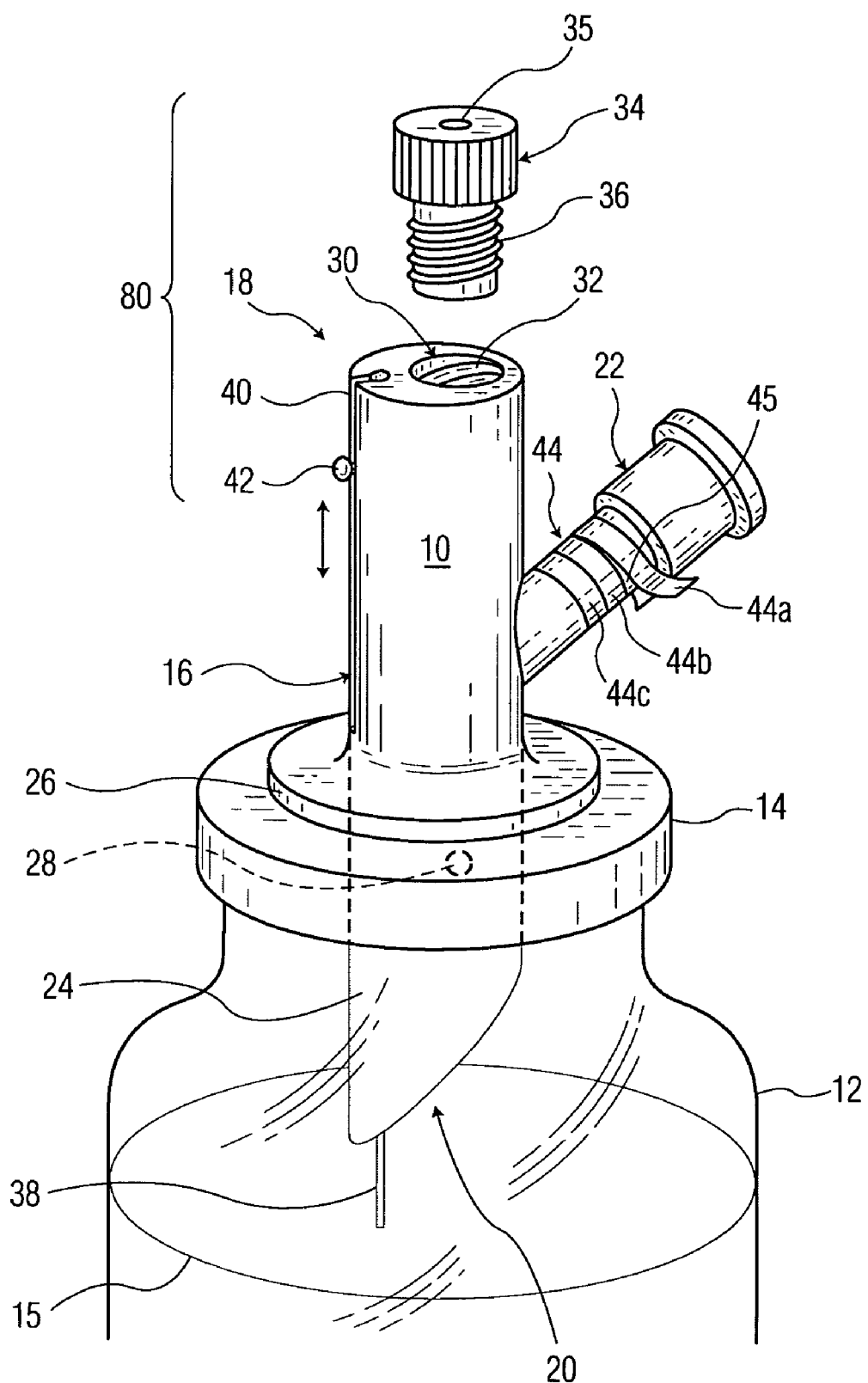
FIG. 1 is a perspective view of a spike assembly mounted on a fluid medication containing vial for various embodiments of the present invention.

With reference to FIG. 1 of the drawings, a spike assembly generally identified by reference numeral 10 is shown for multiple embodiments of the present invention. The spike assembly 10 is designed for coupling with a vial 12 containing a fluid 15 such as, for example, a therapeutic agent. The vial 12 includes a cap 14 that seals the fluid 15, such as, for example, a medication. The cap 14 of the vial 12 may be composed of a metal foil such as, for example, plastic, aluminum or a resilient resealable material such as rubber. The spike assembly 10 includes a body 16 having a top end 18 and a bottom end 20, and an optional vent member 22 for allowing gas to pass between the vial 12 and the ambient as will be further described hereinafter.

The spike assembly 10 can be composed of any suitable rigid material that is at least substantially inert to fluids especially pharmaceutically active agents and the like. The rigid inert material includes plastics, metals, glass and the like. The spike assembly 10 can be fabricated from multiple component parts. It is preferable that the main body of the spike assembly be composed of a single, unitary construction, such as obtained via molded plastic material, for example.

The bottom end 20 includes a piercing portion 24 adapted for piercing through the cap 14. The piercing portion 24 comprises a steeply angled tapered shape that forms a sharp piecing tip. Upon piercing, the piercing portion 24 penetrates through the cap 14 and occupies the interior portion of the vial 12. A flange portion 26 extends around a midportion of the body 16 below the vent member 22, and maintains a flush contact with the top of the vial 12 during coupling engagement. The flange portion 26 ensures that the spike assembly 10 is positioned at a sufficient depth into the vial 12, while minimizing undesirable shifting of the spike assembly 10 in the vial 12 during usage. A drain aperture 28 is located proximate the flange portion 26 on the piercing portion 24 near its entry into the vial 12, as shown, for maximizing the amount of fluid withdrawn from the vial 12 into the fluid conduit 46.

The top end 18 includes an opening 30 having an internal threaded portion 32. A port or cap member 34 having an external threaded portion 36 is adapted for sealing engagement with the opening 30, and is secured by the threaded engagement between the threaded portions 32 and 36 of the opening 30 and the port member 34, respectively. The port member 34 and the opening 30, in combination, form a port structure 80. The port member 34 ensures that the spike assembly 10 remains fluidly sealed to prevent fluid leakage or passage from the vial 12. The port member 34 includes a resealable membrane portion 35 that allows the needle of a hypodermic syringe to be inserted therethrough and sealed about its entry point to enable fluid 15 to be drawn from the vial 14 as will be further described below. It is noted that the port member 34 and the opening 30 can be adapted to include any fluid coupling configurations as known in the art such as, for example, Luer lock coupling configurations, and the like which allows compatible fluid coupling with various fluid passing devices including those having attached needles or those without needles. It is further noted that the port member 34 can be formed as an integral component permanently affixed to the body 16 of the spike assembly 10.

Optionally, the spike assembly 10 can further include a metering pin 38 slidably extendable from the piercing portion 24. The metering pin 38 located within a channel groove 40 includes a small protruding handle portion 42, which can be pushed vertically upward or downward by a user along the outside of the spike assembly 10. Such action causes, the proximal end of the pin 38 to be slidably moved in a vertical direction along the channel groove 40 by the user to actuate the extension or retraction of the metering pin 38 within the vial 12. The operation of the metering pin 38 will be further explained hereinafter.

In one preferred embodiment, the spike assembly 10 further includes a visual indicator 44 composed of a plurality of indicator portions 45 each covered by a strip 44a, 44b or 44c. The indicator portions 45 each can be preprinted with a preassigned color coding and/or indicia, which represent to the user information such as details of the contents of the vial 12, including storage temperature requirements, and/or light sensitivity. One or more specific indicator portions 45 can be selectively revealed by removing one corresponding strip 44a, 44b or 44c depending on the desired indicia and/or color(s) to be revealed. In the preferred embodiment, the indicator portions 45 are used to provide information about storage condition requirements, for example, blue representing refrigeration, yellow representing room temperature or a cool place, and orange representing light sensitivity. Note that the invention is not limited to any particular color or indicia for providing desired visual information.

Figure 2:
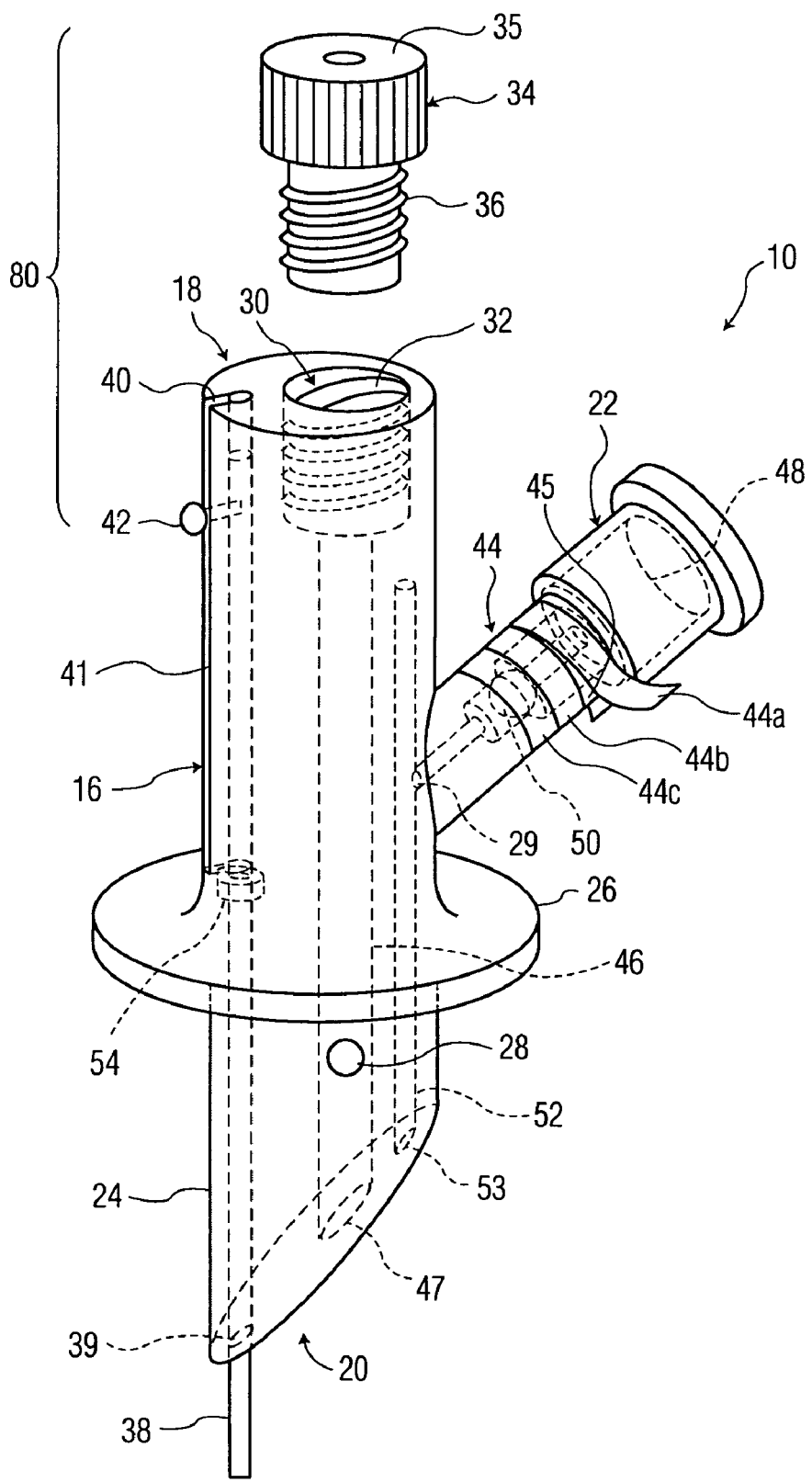
FIG. 2 is a perspective view of the spike assembly with the interior portions thereof drawn in phantom for various embodiments of the present invention.

Referring to FIG. 2, the spike assembly 10 includes a fluid conduit 46 that extends between the opening 32 and an inlet 47 at the bottom end 20. The drain aperture 28 is positioned in fluid communication with the fluid conduit 46. The fluid conduit 46 is configured to facilitate the flow of fluid 15 from the bottom end 20 to the top end 18 of the spike assembly 10. In this manner, a needle of a hypodermic syringe upon insertion into the port member 34 is positioned within the fluid conduit 46 to permitting drawing of the fluid 15 therefrom into an associated syringe. The drain aperture 28 is positioned proximate to the flange portion 26 to permit fluid 15 to drain substantially fully from the vial 12 during operation (i.e., drawing by the syringe) as will be further described hereinafter.

The spike assembly 10 further includes an air conduit 52 extending at least between an inlet 48 of the vent member 22 and an outlet 53 located at the bottom end 20 of the air conduit 52. The air conduit 52 allows the passing of ambient air through the inlet 48, a filtering medium 48a retained in vent member 22 (as shown best in FIG. 5), a vent outlet 29, the air conduit 52, and through the vent outlet 53 into the vial 12, during the dispensing of the fluid 15 as it is drawn into the syringe.

The filtering member 22 further includes a check valve mechanism 50 located between the filter inlet 48 and the air conduit 52. The check valve mechanism 50 operates to allow a one way flow of air from the filter inlet 48 into the vial 12, while preventing passage of the fluid 15 and air in the opposite direction. The check valve mechanism 50 can encompass any one way types valves as known in the art including, for example, ball check valves. This permits the equalization of air pressure between the syringe being filled and the vial 12.

As best shown in FIG. 2, the top portion of the channel groove 40 includes an open slot 41 that extends along the side of the spike assembly 10 to the flange portion 26 and terminates at a resilient grommet 54. The handle portion 42 is slidably movable by the user through the length of the open slot 41. The metering pin 38 is positioned within the channel groove 40 and extends through a pin opening 39 at the bottom end 20 of the spike assembly 10. The user can move the metering pin through the pin opening by operating the handle portion 42. The resilient grommet 54 cooperates with the external surface of the metering pin 38 to ensure a good fluid seal to prevent passing of the fluid 15 from the vial 12 into the open slot 41. The interaction between the resilient grommet 54 and the metering pin 38 provides sufficient frictional force to prevent inadvertent movement once the metering pin 38 is set at a specific position.

Figure 3:
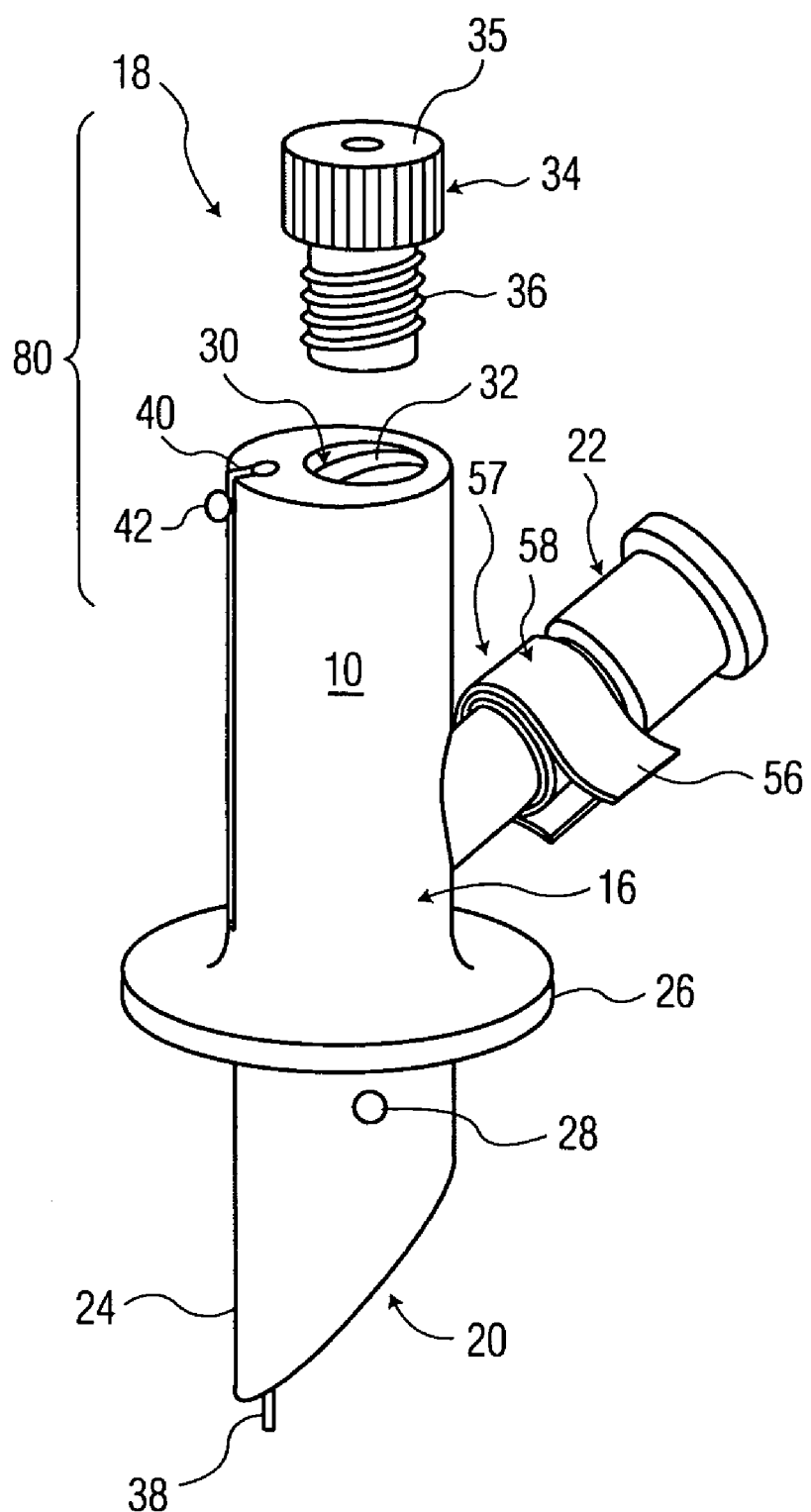
FIG. 3 is a perspective view of a spike assembly shown with a different visual cue component than the embodiment of FIGS. 1 and 2 for an alternative embodiment of the present invention.

Referring to FIG. 3, an alternative embodiment of the spike assembly 10 is shown. The spike assembly 10 includes all the component parts except the visual indicator 44 shown in FIGS. 1 and 2. The spike assembly 10 includes a visual indicator 57 having a single band 58 composed of a plurality of concentrically arranged strips 56. Each of the strips 56 includes different indicia or color scheme representing specific information, for example, as to the content of the vial 12 or a specific storage requirement, such as, for example, temperature range. As an example using a color scheme, blue may signify refrigeration, yellow may signify a room temperature or cool storage, and orange may signify light sensitive. The user can remove each of the concentric strips 56 until the strip 56 containing the desired indicia is exposed.

Figure 4:
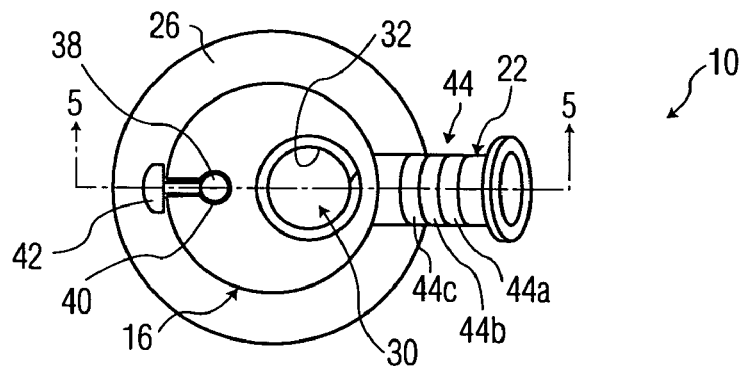
FIG. 4 is a top plan view of the spike assembly of FIG. 1 in accordance with the present invention.
Figure 6:
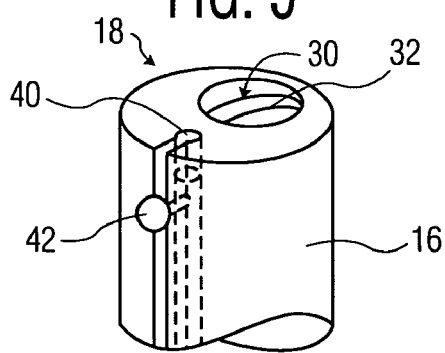
FIG. 6 is an enlarged perspective view of a top portion of the spike assembly of FIG. 1.

Referring to FIGS. 4 and 6, the port member 34 can be threadedly removed from the opening 30 in the event the user needs to dispense the fluid 15 directly from the vial 12 in any known, conventional manner. Alternatively, the port member 34 can be readily replaced with a suitable fluid connector such as, for example, an intravenous drip connector for facilitating continuous dispensing as desired. In addition, the visual indicator 44 is preferably positioned at an appropriate location on the spike assembly 10 to enable the user to see it from various angles.

Figure 5:
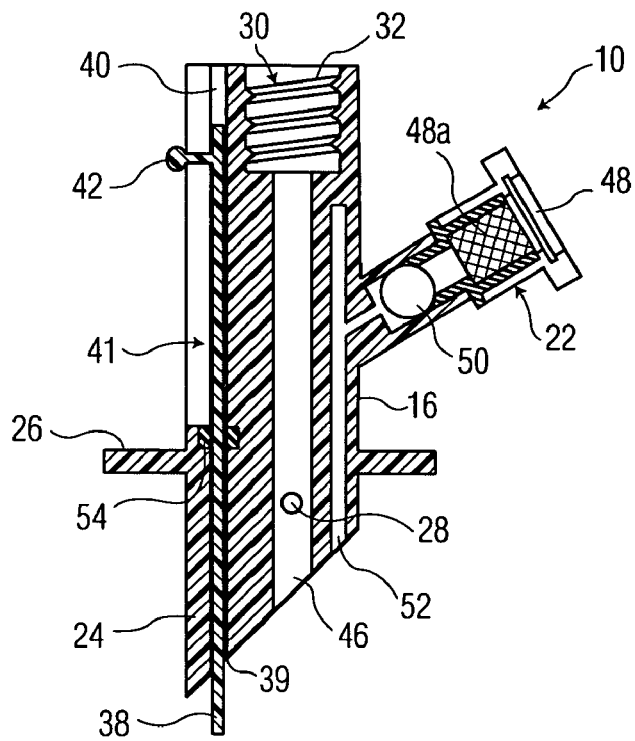
FIG. 5 is a side partial cross sectional view of the spike assembly taken along lines 5—5 of FIG. 4 in accordance with various embodiments of the present invention.

Referring to FIG. 5, a cross sectional view of the spike assembly 10 is shown. The filtering medium 48a in vent 22 is generally composed of a mechanical filter preferably of the type have a pore size that is sufficiently small to prevent passage of undesirable contaminants including, but not limited to, pathogens, bacteria, dust, spores, mold, viruses, dirt, and the like. The filtering medium 48a may further include other filter materials that are chemically active such as activated charcoal materials or desiccants that can further prevent other undesirable contaminants from entering the spike assembly 10 and ultimately into the vial 15. The fluid conduit 46 and the air conduit 52 are preferable arranged separately and at a distance from one another to prevent unintentional drawing of the air along with the fluid 15 to be dispensed.

The metering pin 38 can be extended or retracted through the pin opening 39 by moving the handle portion 42. The metering pin 38 assists the user by providing a visual cue as a full volume marker. This feature allows the user to visually estimate to the number of doses or volume of the fluid 15 remaining within the vial 12. The metering pin 38 allows the using to mark the initial volume of the fluid 15. During operation, the end of the metering pin 38 is extended down to the full volume level of the fluid 15 with the vial 12 in the upright position. Once the meter pin 38 is set at the full volume mark, it remains in the same position. The user draws the fluid 15 by the hypodermic syringe in the usual manner, until the desired dosage is obtained. The user returns the vial 12 to the upright position and thus is able to visually determine the volume or number dosages of the fluid 15 is remaining by comparing the full volume position of metering pin 38 with the current level of the fluid 15 in the vial 12. Accordingly, the user can estimate visually how much volume is remaining in the vial 12 for greater inventory prediction.

Figure 7:
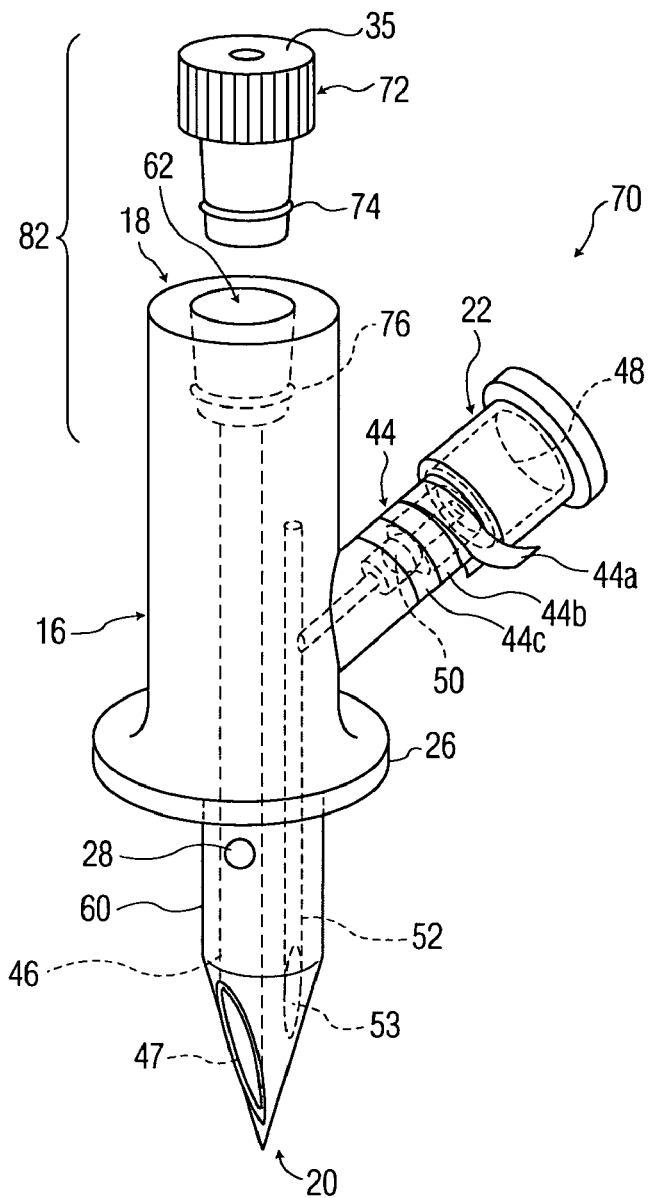
FIG. 7 is a perspective view of a spike assembly using a Luer lock type fitting for another embodiment of the present invention.

Referring to FIG. 7, a spike assembly 70 is shown for another embodiment of the present invention. The spike assembly 70 includes the same components as the spike assembly 10 of FIG. 2 except for a different configuration for a port member 72 and an opening 62, and for a piecing portion 60, in addition, to the absence of a metering pin 38. The port member 72 and the opening 62, in combination, form a port structure 82 at the top end 18. The port member 72 comprises a tapered fitting for coupling with the corresponding tapered opening 62 to produce a snug sealing fit therebetween. The port member 72 further comprises a circular protrusion 74 which is configured to be seated within a corresponding circular groove 76 of the opening 62 to form a fluid seal fit therebetween. The tapered opening 62 in adapted to receive a standard syringe having a similarly tapered fluid port to permit the syringe to be filled with medication in the absence of an attached needle. Note also that the configuration of the port structure 82 shown herein can be interchanged with the port structure 80 of FIGS. 1 to 6. In addition, the piercing portion 60 of the spike assembly 70 can also be interchanged with the piercing portion 24 of FIGS. 1 to 6.

Figure 7A:
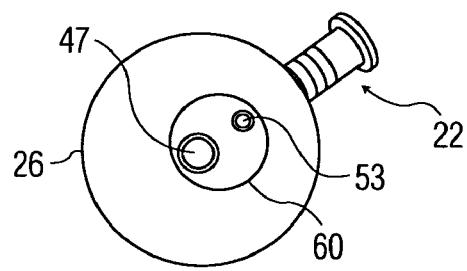
FIG. 7A is a bottom plan view of the spike assembly of FIG. 7.

Referring to FIG. 7A, a bottom plan view of the spike assembly 70 is shown. The inlet 47 of the fluid conduit 46 and the outlet 53 of the air conduit 52 are located at opposing sections of the piercing portion 60.

Figure 8:
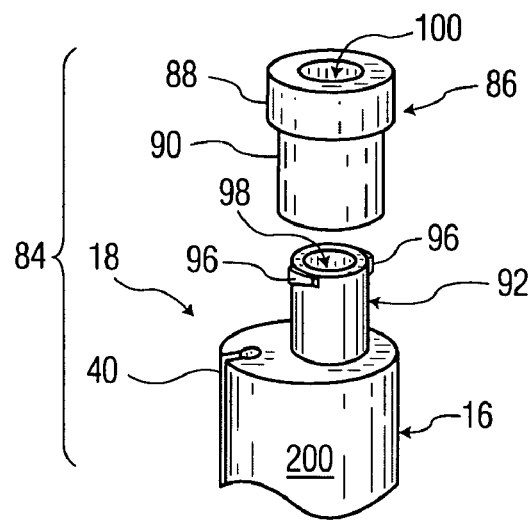
FIG. 8 is an assembly view of a port structure of a spike assembly for another embodiment of the present invention.
Figure 9:
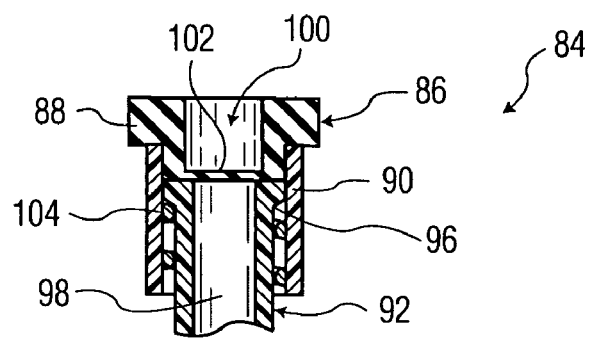
FIG. 9 is a cross sectional view of the port structure with the port member secured to the open extension in accordance with the present invention.
Figure 10:
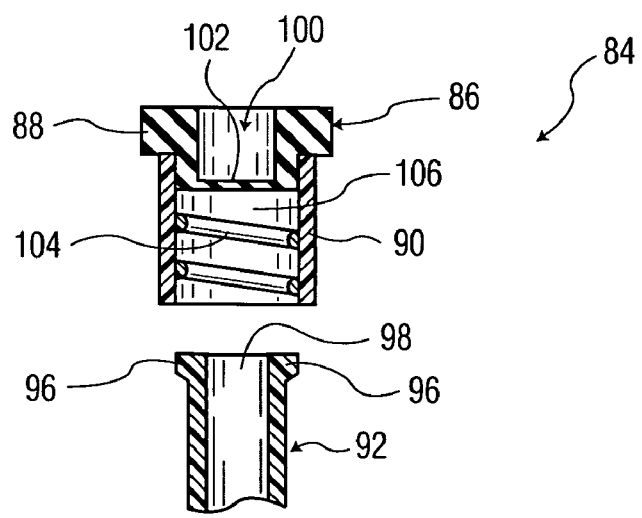
FIG. 10 is a cross sectional view of the port structure with the port member shown unsecured from the open extension in accordance with the present invention.
Figure 11:
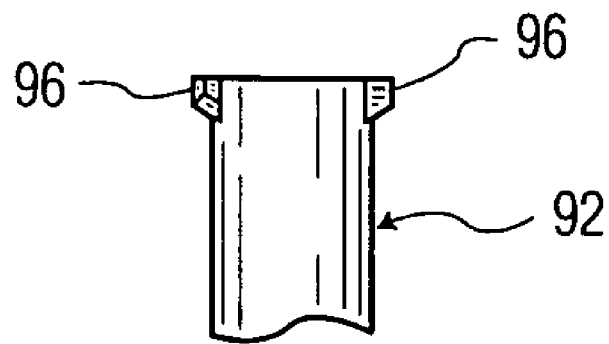
FIG. 11 is a perspective view of the open extension of the spike assembly.
Figure 12:
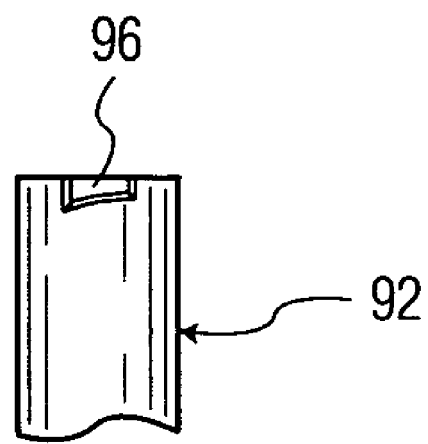
FIG. 12 is a perspective view of the open extension rotated 90° about its vertical axis in accordance with the present invention.

Referring to FIG. 8, a port structure 84 located at the top end 18 of a spike assembly 200 is shown for another embodiment of the present invention. The port structure 84 includes a Luer lock construction for enabling fluid coupling with Luer lock type syringes or other similarly configured fluid drawing devices. The port structure 84 includes a port member 86 having an upper portion 88 and a lower portion 90, and an open extension 92 with a pair of locking tabs 96 and an opening 98 in fluid communication with the fluid conduit 46. The upper portion 88 is composed of a resilient material such as rubber, and the lower portion 90 is composed of a rigid material. The port structure 84 is adapted to facilitate fluid coupling with hypodermic syringes with or without an attached needle.

The port member 86 is adapted for Luer lock fluid coupling engagement with the open extension 92. The port member 86 is adapted to permit the needle of a hypodermic syringe to be passed into the open extension 92 for dispensing fluid through the spike assembly 200. Alternatively, the port member 86 can be removed from the open extension 92 for coupling with a hypodermic syringe without an attached needle. The open extension 92 is adapted to fluidly couple with a corresponding Luer lock configured fluid port of a needleless syringe (not shown) to permit dispensing of the fluid through the spike assembly 200. It is noted that the open extension 92 is further adapted to receive a standard syringe having a typical "slip fit" fluid port for fluid coupling.

Referring to FIGS. 9 through 12, the port member 86 includes a central top cavity 100, a membrane portion 102, and central bottom cavity 106 with internal threads 104. The central bottom cavity 106 is adapted to reversibly receive the open extension 92 for engagement therebetween and seal in the opening 98 of the extension 92 from ambient. The internal threads 104 are adapted to threadedly engage the locking tabs 96 of the open extension 92. The port member 86 is securable to open extension 92 with the twist of a turn clockwise to engage the locking tabs 96 with the threads 104. The locked engagement between the locking tabs 96 and the threads 104 biases the upper portion 88 of the port member 86 against the top edge portion of the open extension 92 to produce a fluid seal, thereby preventing any fluid leakage. With the port member 86 coupled to the extension 92, a hypodermic needle can be passed through the central cavity 100 and pierced through the membrane portion 102 into the opening 98. The resilient membrane portion 102 is composed of a resilient material that allows a hypodermic needle to penetrate it, while maintaining a fluid seal during and after dispensing.

With reference to FIGS. 1, 2, 4, and 5 through 12, the operation of the spike assembly will now be described in general. The spike assembly 10 can be fabricated in a form suitable for disposable one time use in order to ensure sterility and minimize contamination during use. The rubber cap 14 of the vial 12 is wiped with an antiseptic. The spike assembly 10 is thereafter mounted to the vial 12 by pushing the piercing portion 24 through the cap 14 of the vial 12 until the flange portion 26 comes into contacts with the cap 14. Optionally, the user may operate the metering pin 38 by moving the handle portion 42 downward until the tip the metering pin 38 into contact with the surface of the fluid 15. Once set, the metering pin 38 is maintained statically in position through frictional interaction between the metering pin 38 and the grommet 54.

The user thereafter obtains a clean and sterile hypodermic syringe. The port member 35 may be removed to allow the spike assembly 10 to receive the fluid port of the hypodermic syringe without an attached needle. Otherwise the port member 35 remains coupled to the opening 30 and the hypodermic needle of the syringe may be inserted through the resilient resealable membrane portion 35 of the port member 34. The vial 12, the spike assembly 10 and the hypodermic syringe are then upturned bottom side up to allow the fluid 15 to fill the fluid conduit 46 of the spike assembly 10. The syringe plunger is then drawn back until the appropriate line for the dosage is reached. If the piercing portion 24 is above fluid level (i.e., low fluid level), the fluid 15 is simply drained through the drain aperture 28 into the fluid conduit 46 to minimize waste and avoid the need to manipulate the needle within the vial 15 to get at the fluid 15.

For needleless syringes, the port member 34 is removed from the opening 30 to receive the fluid port of the syringe. Thereafter, the fluid is dispensed from the vial 12 in the same manner as described above.

Alternatively, as previously mentioned relative to the embodiment of FIG. 7, if the needleless syringe has a tapered fluid port without a needle attached thereto, it can be directly coupled with the spike assembly 10 at the tapered opening 30 (see FIG. 7) for drawing fluid. For use with a needle equipped syringe, the port member 72 can be replaced in the opening 30 with the needle inserted the through a resealable membrane portion 35 into the fluid conduit 46 for withdrawing fluid therefrom.

Alternatively, as previously mentioned relative to the embodiment of FIG. 8, if the needleless syringe has a Luer lock fluid port without a needle attached thereto, it can be directly coupled with the spike assembly 10 at the corresponding Luer lock open extension 92 (see FIG. 8) for drawing fluid. For use with a needle equipped syringe, the port member 86 can be coupled with the open extension 92 with the needle inserted the through sealable membrane portion 88 via the cavity 100 into the fluid conduit 46 for withdrawing fluid therefrom.

As the fluid is drawn into the syringe, ambient air is drawn through the filter member 22 to take up the vacuum in the vial 12 generated by the syringe. Upon completion of the dispensing, the syringe can then be withdrawn from the vial 12. The vial 12 and spike assembly 10 are returned to a suitable storage area in the upright position. Optionally, the user may check the metering pin 38 to visually determine the volume dispensed.

Although various embodiments of the invention have been shown and described, they are not meant to be limiting. Those of skill in the art may recognize various modifications to these embodiments, which modifications are meant to be covered by the spirit and scope of the appended claims. For example, the present invention is not limited to vials, but can also be utilized with intravenous bags, and the like.

What is claimed is:

1. A spike assembly for facilitating the supply of a fluid from a container to a fluid drawing device including a hypodermic syringe, said spike assembly comprising:
    a body having a first bottom end and a second top end, and a fluid conduit extending between the first and second ends;
    a piercing member located at the first end for piercing into the container to form a fluid sealing engagement, said piercing member further including a fluid drawing device such as a drain aperture for passing the fluid into the first end from the container into the fluid conduit; and
    an opening located at the second top end for receiving a fluid port or a needle of the fluid drawing device to enable the fluid drawing device to draw the fluid from the container via the fluid conduit, and a resealable membrane portion providing a fluid seal about the fluid port where it passes through the receiving means;
    a vent extending through the body in fluid communication with an ambient for facilitating passage of a gas between the container and the ambient during operation;
    means for communicating to a user details corresponding to the fluid contained in the container, said means comprising at least one removable band located circumferentially around an outside surface of said vent and having preprinted indicia on said band that corresponds to a temperature requirement to the fluid contained in the container;
    wherein the at least one removable band comprises a plurality of bands having a removable protective cover strip disposed over the at least one removable band.

2. The spike assembly of claim 1, wherein the vent further comprises a filter.

3. The spike assembly of claim 1, wherein the receiving means is a Luer lock compatible port.

4. The spike assembly of claim 1, wherein the receiving means further comprises a resealable membrane port.

5. The spike assembly of claim 4, wherein the resealable membrane port is in the form of a cap removably mounted to the second end of the body.

6. The spike assembly of claim 5, wherein the cap and the second end of the body are reversibly coupled via a Luer lock coupling engagement.

7. The spike assembly of claim 1, wherein the body further comprises a flange extending radially therearound for flush placement on the top of the container during operation.

8. The spike assembly of claim 1, wherein the fluid passing means further comprises a drain aperture positioned near the point of entry inside the container, said drain aperture being in fluid communication with the fluid conduit.

9. The spike assembly of claim 1, further comprising a retractable pin extendable from the piercing member.

10. A spike assembly for facilitating the supply of a fluid from a container to a fluid drawing device including a hypodermic syringe, said spike assembly comprising:

a body having a first bottom end and a second top end, and a fluid conduit extending between the first and second ends;

a piercing member located at the first end for piercing into the container to form a fluid sealing engagement, said piercing member further including a fluid drawing device such as a drain aperture for passing the fluid into the first end from the container into the fluid conduit;

an opening located at the second top end for receiving a fluid port or a needle of the fluid drawing device to enable the fluid drawing device to draw the fluid from the container via, the fluid conduit, and a resealable membrane position providing a fluid seal about the fluid port where it passes through the receiving means; and a vent extending through the body for venting gas between ambient and the interior portion of the container during operation, means for communicating to a user details corresponding to the fluid contained in the container, said means comprising at least one removable band located circumferentially around an outside surface of said vent and having preprinted indicia on said band that corresponds to a temperature requirement to the fluid contained in the container;

wherein the at least one removable band comprises a plurality of bands having a removable protective cover strip disposed over the at least one removable band.

11. A spike assembly for facilitating the supply of a fluid from a container to a fluid drawing device including a hypodermic syringe, said spike assembly comprising:

a body having a first bottom end and a second top end, and a fluid conduit extending between the first and second ends;

a piercing member located at the first end for piercing into the container to form a fluid sealing engagement, said piercing member further including a fluid drawing device such a drain aperture for passing the fluid into the first end from the container into the fluid conduit;

an opening located at the second top end for receiving a fluid port or a needle of the fluid drawing device to enable the fluid drawing device to draw the fluid from the container via the fluid conduit, and a resealable membrane portion providing a fluid seal about the fluid port where it passes through the receiving means;

a vent extending through the body in fluid communication with an ambient for facilitating passage of a gas between the container and the ambient during operation;

means for communicating to a user details corresponding to the fluid contained in the container, said means comprising at least one removable band located circumferentially around an outside surface of said vent and having preprinted indicia on said band that corresponds to a temperature requirement to the fluid contained in the container;

wherein the at least one removable band comprises a plurality of bands having a removable protective cover strip disposed over the at least one removable band.

* * * * *